(12) United States Patent
Ballantyne et al.

(10) Patent No.: US 8,056,148 B1
(45) Date of Patent: Nov. 15, 2011

(54) SHOWER/GLOVE SYSTEM (76) Inventors: Evan Ballantyne, Orlando, FL (US); Anthony D. Cooprider, Rochester Hills, MI (US)

( * ) Notice: Subject to any disclaimer, the term of this patent is extended or adjusted under 35 U.S.C. 154(b) by 147 days.

(21) Appl. No.: 12/380,118

(22) Filed: Feb. 24, 2009

Related U.S. Application Data (63) Continuation-in-part of application No. 11/541,967, filed on Oct. 2, 2006, now abandoned.

(60) Provisional application No. 60/727,087, filed on Oct. 14, 2005.

(51) Int. Cl.
*A41D 19/00* (2006.01)
*A41D 27/02* (2006.01)

(52) U.S. Cl. .......... 2/161.7; 2/161.6; 2/168; 2/159; 2/158; 2/160

(58) Field of Classification Search .......... None
See application file for complete search history.

(56) References Cited

U.S. PATENT DOCUMENTS

| | | | |
|---|---|---|---|
| 2,224,871 A | 6/1941 | Guinzburg | |
| 4,845,780 A * | 7/1989 | Reimers et al. | 2/160 |
| 4,918,754 A * | 4/1990 | Leatherman et al. | 2/16 |
| 4,924,530 A * | 5/1990 | Tagaya | 2/163 |
| 5,020,159 A * | 6/1991 | Hellickson | 2/158 |
| 5,063,919 A * | 11/1991 | Silverberg | 602/3 |
| 5,366,204 A | 8/1994 | Matys | |
| 5,357,636 A * | 10/1994 | Dresdner et al. | 2/161.7 |
| 5,442,816 A * | 8/1995 | Seketa | 2/161.7 |
| 5,592,953 A * | 1/1997 | Delao | 128/882 |
| 5,643,183 A * | 7/1997 | Hill | 602/3 |
| 5,720,713 A * | 2/1998 | Hutchison | 602/3 |
| 5,734,992 A * | 4/1998 | Ross | 2/161.7 |
| 6,029,275 A | 2/2000 | De Prado | |
| 6,267,115 B1 * | 7/2001 | Marshel | 128/877 |
| 6,276,365 B1 | 8/2001 | Warner | |
| 6,892,735 B2 | 5/2005 | Clinton | |
| 6,895,971 B1 * | 5/2005 | Evans | 128/869 |
| 6,916,301 B1 * | 7/2005 | Clare | 602/3 |
| 7,290,290 B2 * | 11/2007 | Treadway Fancher | 2/16 |
| 7,448,091 B2 * | 11/2008 | Kruss | 2/161.7 |

* cited by examiner

*Primary Examiner* — Bobby Muromoto, Jr.

(57) ABSTRACT

A glove fabricated of a polyethylene has a distal portion in a shape to accommodate a hand. A proximal portion of the glove formed as an extension of the distal portion has a length between 150 percent and 175 percent of the length of the distal portion. A polyethylene tab and a strap form a seal on the proximal portion of the glove. The tab is integrally formed with the glove. The strap is fabricated of elastic bandage material and has an attached end coupled to the tab with a semi-adhesive property for removably coupling the strap to itself.

1 Claim, 6 Drawing Sheets

SHOWER/GLOVE SYSTEM

RELATED APPLICATION

The present application is a continuation-in-part application of pending application Ser. No. 11/541,967 filed Oct. 2, 2006 now abandoned which is, in turn, based upon Provisional Application Ser. No. 60/727,087 filed Oct. 14, 2005, the subject matter of which prior applications is incorporated herein by reference.

BACKGROUND OF THE INVENTION

1. Field of the Invention

The present invention relates to a shower glove protector system and more particularly pertains to protecting the hand and arm of a patient with at least one site of interest during showering and bathing.

2. Description of the Prior Art

The use of protector systems of known designs and configurations is known in the prior art. More specifically, protector systems of known designs and configurations previously devised and utilized for the purpose of protecting a user through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 2,244,871 issued Jun. 10, 1941 to Guinzburg relates to a Waterproof Protective Device. U.S. Pat. No. 5,336,204 issued Aug. 9, 1994 to Matys relates to a Protective Cover for an Infusion Device. U.S. Pat. No. 5,592,953 issued Jan. 14, 1997 to Delao relates to a Tubular Sleeve with Elasticized Sealing Means. U.S. Pat. No. 6,267,115 issued Jul. 31, 2001 to Marshel relates to an Intravenous Protecting Device. U.S. Pat. No. 6,276,365 issued Aug. 21, 2001 to Warner relates to a Protective Sleeve for a Chronically Implanted Intravenous Site. U.S. Pat. No. 6,892,735 issued May 17, 2005 to Clinton relates to an IV Sleeve. U.S. Pat. No. 5,734,992 issued Apr. 7, 1998 to Ross relates to a Protective Hand and Arm Covering Article. Lastly, U.S. Pat. No. 6,029,275 issued Feb. 29, 2000 to De Prado relates to a Protective Glove for Use with Nylon Sotckings and Other Snag Prone Garments.

While these devices fulfill their respective, particular objectives and requirements, the aforementioned patents do not describe a shower glove protector system that protects the hand and arm of a patient with at least one site of interest during showering and bathing.

In this respect, the shower glove protector system according to the present invention substantially departs from the conventional concepts and designs of the prior art, and in doing so provides an apparatus primarily developed for the purpose of protecting the hand and arm of a patient with at least one site of interest during showering and bathing.

Therefore, it can be appreciated that there exists a continuing need for a new and improved shower glove protector system which can be used for protecting the hand and arm of a patient with at least one site of interest during showering and bathing. In this regard, the present invention substantially fulfills this need.

SUMMARY OF THE INVENTION

In view of the foregoing disadvantages inherent in the known types of protector systems of known designs and configurations now present in the prior art, the present invention provides an improved shower glove protector system. As such, the general purpose of the present invention, which will be described subsequently in greater detail, is to provide a new and improved shower glove protector system and method which has all the advantages of the prior art and none of the disadvantages.

To attain this, the present invention essentially comprises a shower glove protector system. First provided is a glove. The glove has a distal portion. The distal portion is in the shape of a hand. The distal portion is formed with four fingers. The four fingers includes a little finger, a fourth finger, a middle finger and an index finger. The glove also includes a thumb. The distal portion has varying widths essentially along its entire length.

The glove has a proximal portion. The proximal portion has a proximal end and a distal end. The proximal end is open for the receipt and passage of a hand, forearm, elbow and a portion of an upper arm of a patient. The distal end is formed as an extension of the distal portion for the receipt and passage of a hand of a patient. The proximal portion has an essentially common cross sectional configuration along essentially its entire length prior to being worn by a patient.

A common central axis has a proximal extent. The proximal end extends through the proximal portion of the glove. The common central axis has a distal extent. The distal extent extends through the distal portion of the glove including the middle finger. The proximal extent of the central axis of the glove has a length of between about 10 and 14 inches. The distal extent of the central axis of the glove has a length of between about 7 and 9 inches. The proximal portion of the glove is between about 125 percent and 175 percent of the length of the distal portion of the glove. The glove is fabricated of a transparent polyethylene. The polyethylene has a thickness of between about 0.003 inches and 0.012 inches.

Provided last is a security seal. The security seal is provided at the proximal end of the proximal portion of the glove. The security seal includes a fold. The fold is formed by an inward turn of the proximal end of the proximal portion of the glove. The glove has two space circumferential lines of stitching. In this manner an end tunnel is formed. Also in this manner intermediate tunnel is formed. The intermediate tunnel is located between the end tunnel and the proximal end of the proximal portion of the glove. The security seal also includes a elastic band. The elastic band is fabricated of rubber. The elastic band is provided in a cylindrical configuration. The elastic band is located within the intermediate tunnel. In this manner the passage of water introduced through showering and bathing to a location of a patient beneath the glove may be abated. A site of interest is provided. The site of interest is covered by the glove. The length of the elastic band in a relaxed state is between about 8 and 16 inches.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is, therefore, an object of the present invention to provide a new and improved shower glove protector system which has all of the advantages of the prior art protector systems of known designs and configurations and none of the disadvantages. It is another object of the present invention to provide a new and improved shower glove protector system which may be easily and efficiently manufactured and marketed.

It is further object of the present invention to provide a new and improved shower glove protector system which is of durable and reliable constructions.

An even further object of the present invention is to provide a new and improved shower glove protector system which is susceptible of a low cost of manufacture with regard to both materials and labor, and which accordingly is then susceptible of low prices of sale to the consuming public, thereby making such shower glove protector system economically available to the buying public.

Even still another object of the present invention is to provide a shower glove protector system for protecting the hand and arm of a patient with at least one site of interest during showering and bathing.

Lastly, it is an object of the present invention to provide a new and improved shower/glove system having a glove fabricated of a polyethylene with a distal portion in a shape to accommodate a hand, the glove having a proximal portion formed as an extension of the distal portion, the proximal portion having a length between 150 percent and 175 percent of the length of the distal portion, and a seal formed on the proximal portion of the glove including a polyethylene tab integrally formed with the glove and further including a strap fabricated of elastic bandage material having an attached end coupled to the tab and having a semi-adhesive property for removably coupling the strap to itself.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figures 1, 2:
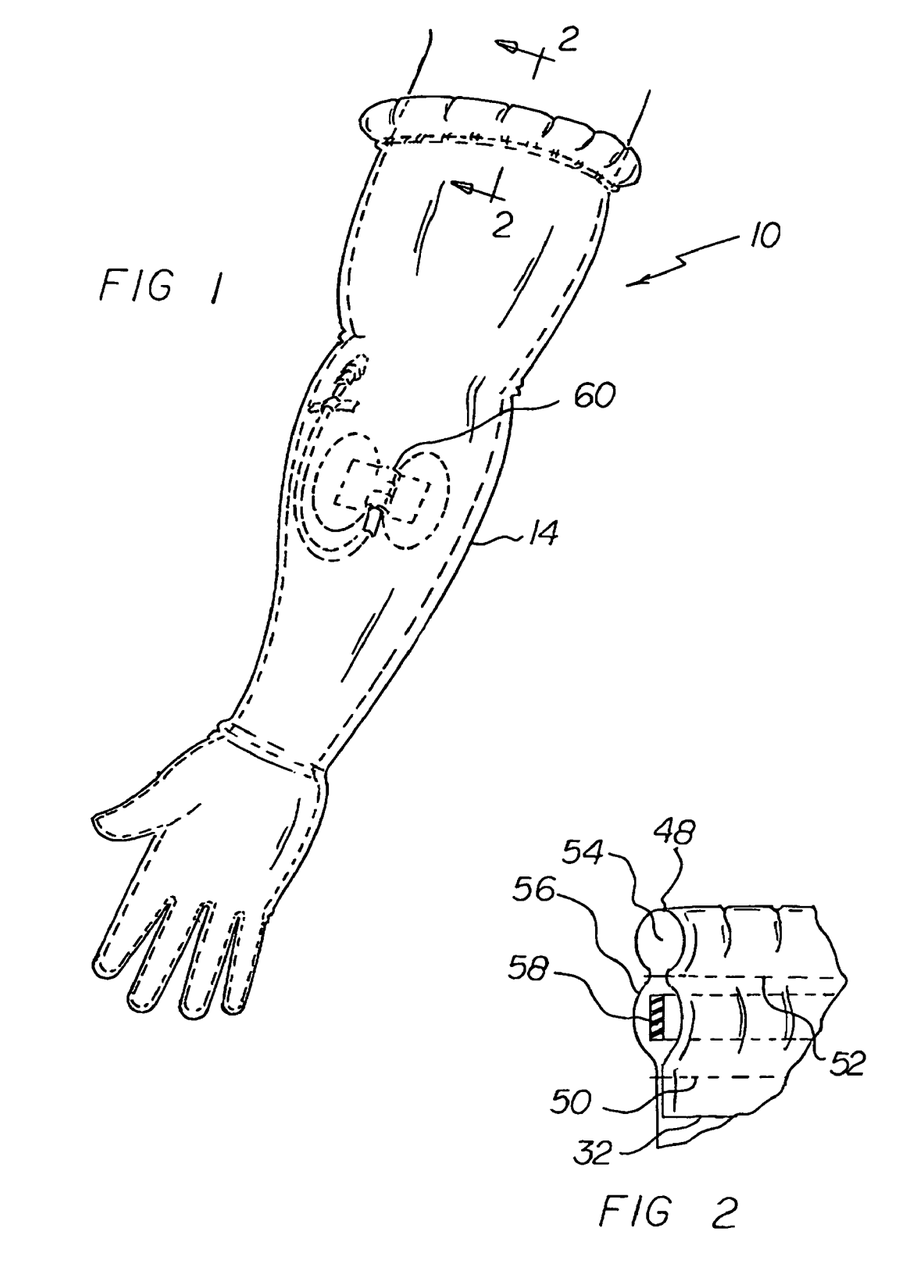
FIG. 1 is a perspective illustration of a shower glove protector system constructed in accordance with the principles of the present invention.
FIG. 2 is a cross sectional view of the system taken along line 2-2 of FIG. 1.

With reference now to the drawings, and in particular to FIG. 1 thereof, the preferred embodiment of the new and improved shower glove protector system embodying the principles and concepts of the present invention and generally designated by the reference numeral 10 will be described.

The present invention, the shower glove protector system 10 is comprised of a plurality of components. Such components in their broadest context include a glove, an axis and a security seal. Such components are individually configured and correlated with respect to each other so as to attain the desired objective.

Figure 3:
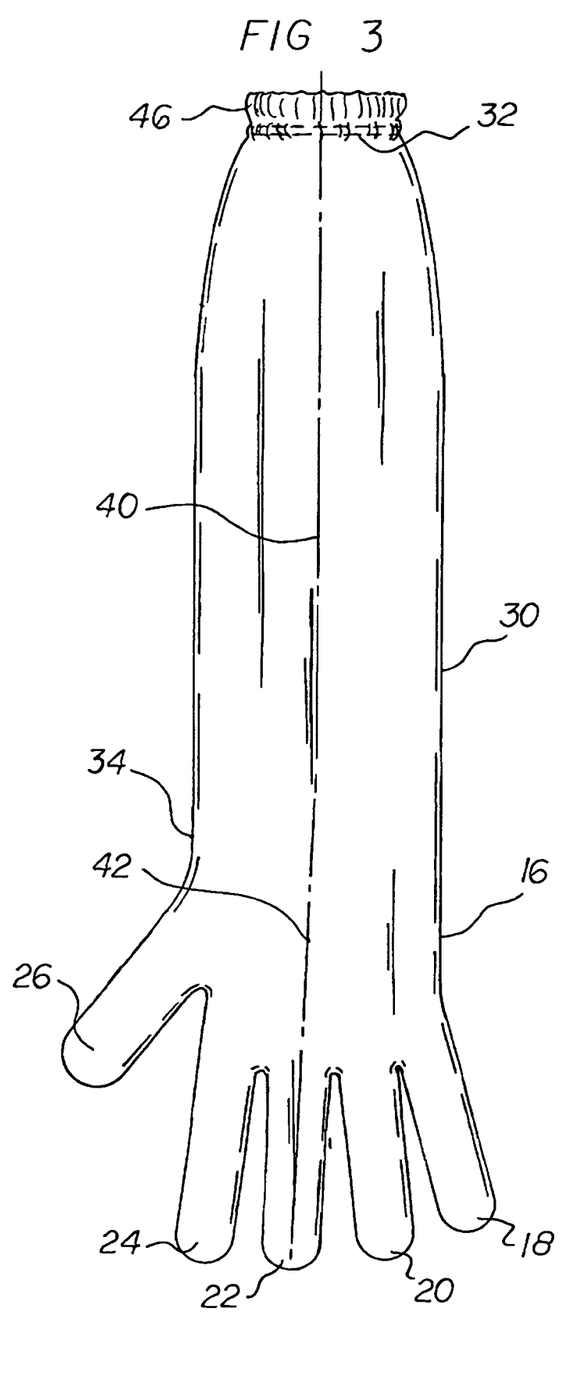
FIG. 3 is a front elevational view of the system shown in the prior Figures.
Figure 4:
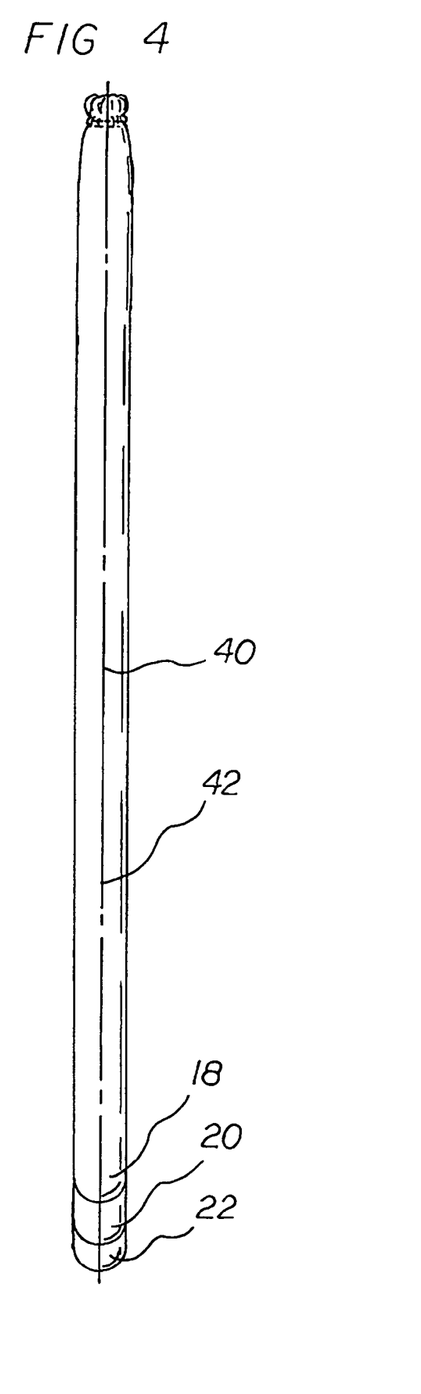
FIG. 4 is a right side elevational view of the system shown in the prior Figures.

First provided is a glove 14. The glove has a distal portion 16. The distal portion is in the shape of a hand. The distal portion is formed with four fingers. The four fingers includes a little finger 18, a fourth finger 20, a middle finger 22 and an index finger 24. The glove also includes a thumb 26. The distal portion has varying widths essentially along its entire length. Note the lower portion of FIG. 3. The glove has a proximal portion 30. The proximal portion has a proximal end 32 and a distal end 34. The proximal end is open for the receipt and passage of a hand, forearm, elbow and a portion of an upper arm of a patient. The distal end is formed as an extension of the distal portion for the receipt and passage of a hand of a patient. The proximal portion has an essentially common cross sectional configuration along essentially its entire length prior to being worn by a patient. Note the upper portion of FIG. 3.

A common central axis has a proximal extent 40. The proximal end extends through the proximal portion of the glove. The common central axis has a distal extent 42. The distal extent extends through the distal portion of the glove including the middle finger. The proximal extent of the central axis of the glove has a length of between about 10 and 14 inches. The distal extent of the central axis of the glove has a length of between about 7 and 9 inches. The proximal portion of the glove is between about 125 percent and 175 percent of the length of the distal portion of the glove. The glove is fabricated of a transparent polyethylene. The polyethylene has a thickness of between about 0.003 inches and 0.012 inches.

Provided last is a security seal 46. The security seal is provided at the proximal end of the proximal portion of the glove. The security seal includes a fold 48. The fold is formed by an inward turn of the proximal end of the proximal portion of the glove. The glove has two space circumferential lines of stitching 50, 52. In this manner an end tunnel 54 is formed. Also in this manner intermediate tunnel 56 is formed. The intermediate tunnel is located between the end tunnel and the proximal end of the proximal portion of the glove. The security seal also includes a elastic band 58. The elastic band is fabricated of rubber. The elastic band is provided in a cylindrical configuration. The elastic band is located within the intermediate tunnel. In this manner the passage of water introduced through showering and bathing to a location of a patient beneath the glove may be abated. A site of interest 60 is provided. The site of interest is covered by the glove. The length of the elastic band in a relaxed state is between about 8 and 16 inches.

The primary embodiment of the invention is shown as a glove covering a site of interest of a patient which includes one type of medical device. It should be understood that the protection afforded by the present invention is intended to include the shielding of a patient's intravenous catheter, IV, and a peripheral inserted central catheter, PICC, and post operative surgical dressing or arm/hand or finger casts when bathing or showering.

Figure 5:
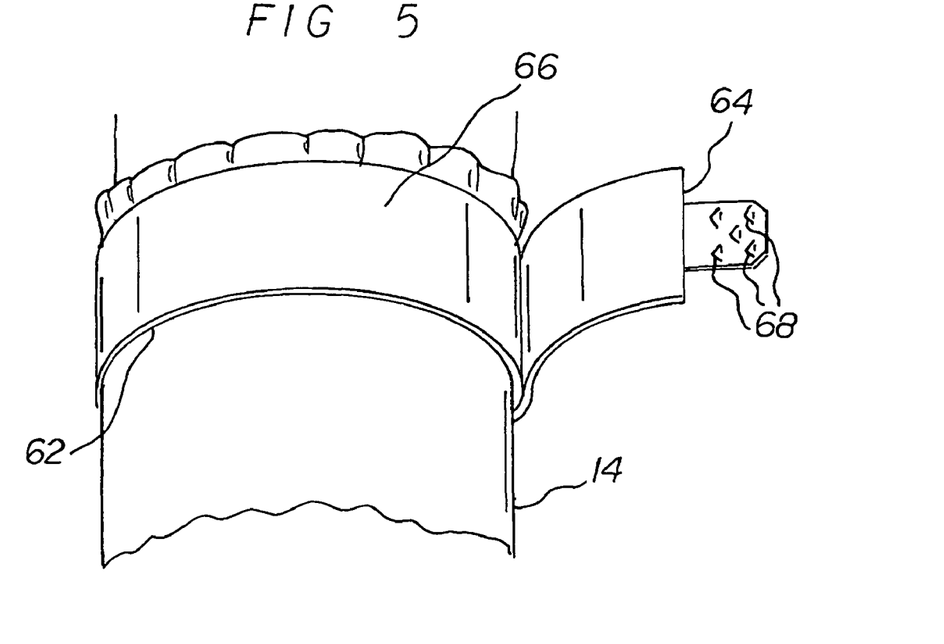
FIG. 5 is a perspective illustration of the upper portion of a shower glove protector system constructed in accordance with an alternate embodiment of the present invention.

As may be seen in the alternate embodiment of FIG. 5, the invention includes a strap of limited elasticity. The security seal includes a strap 62. The strap is fabricated of a material with limited elasticity. The strap is adapted to be wrapped around the upper proximal end of the proximal portion of the glove. The strap has a free end 64 and an intermediate extent 66. The free end has projections 68. The projections are adapted to pierce the intermediate extent. In this manner the strap may be held to abate passage of water introduced through showering and bathing to a location of a patient beneath the glove and at site of interest.

Figure 6:
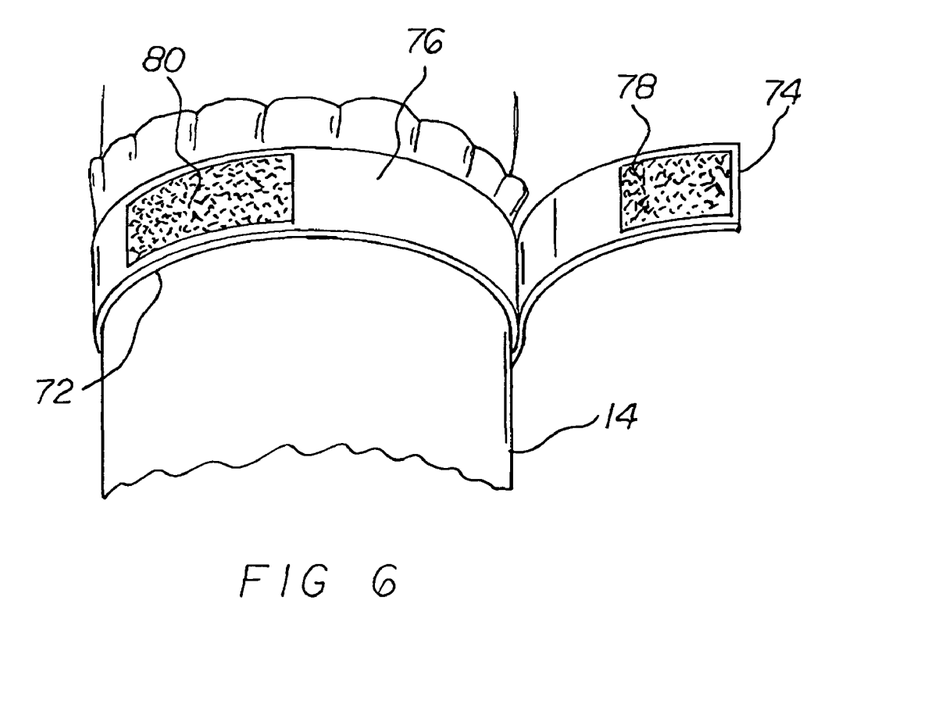
FIG. 6 is a perspective illustration of the upper portion of a shower glove protector system constructed in accordance with another alternate embodiment of the present invention.

As may be seen in the second alternate embodiment of FIG. 6 the invention includes a flexible strap. The security seal includes a strap 72. The strap is fabricated of a flexible material. The strap is adapted to be wrapped around the upper proximal end of the proximal portion of the glove. The strap has a free end 74 and an intermediate extent 76. The free end has a hook and loop fastener 78. A facing part of the intermediate extent also has a hook and loop fastener 80. The hook and loop fasteners of the free end and end extents are adapted to releasably couple for holding the strap to abate passage of water introduced through showering and bathing to a location of a patient beneath the glove and at site of interest.

Figure 7:
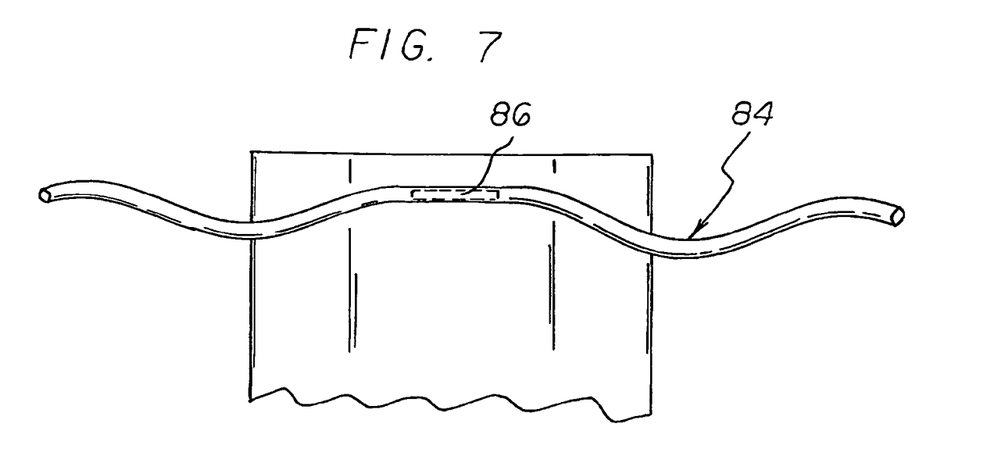
FIGS. 7 and 7A illustrate a third alternate embodiment of the invention wherein the attachment and sealing components are permanently attached at one end of the glove and not separate from it.
Figure 7A:
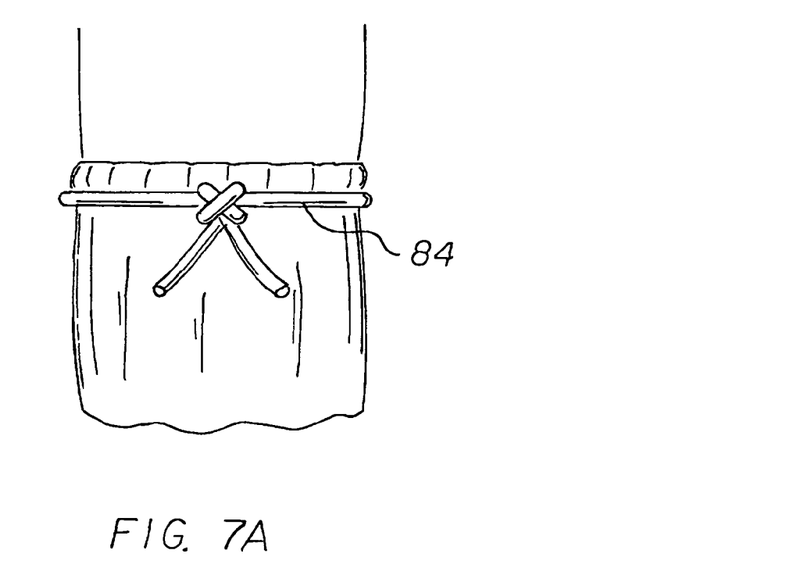

FIGS. 7 and 7A illustrate a third alternate embodiment of the invention, FIG. 7 is when untied and not in use. FIG. 7A is when tied and in use. In such embodiment, the attachment and sealing component 84 is shown as a tie strap which is permanently attached to one end of the glove at a central extent of the strap, preferably by an adhesive 86. Such component is not separate from the glove. The seal includes a folding seal embodiment which is illustrated in FIGS. 1-4 as well as a non-folding seal embodiment. The non-folding seal embodiment employs Coban™ elastic self-adhering medical bandaging tape, which does not require a fold. Coban is a trademark of Minnesota Mining and Manufacturing of Saint Paul, Minn. It employs a constrictive type of seal strap. The security seal is adapted to be accomplished several ways including Coban and Ace™ bandages which adhere to themselves. Ace is a trademark of Beckon Dickinson and Company of Franklin Lakes, N.J. Further embodiments include a hook an loop fasteners as well as rubber straps. These embodiments are illustrated in FIGS. 5-8.

Figure 8:
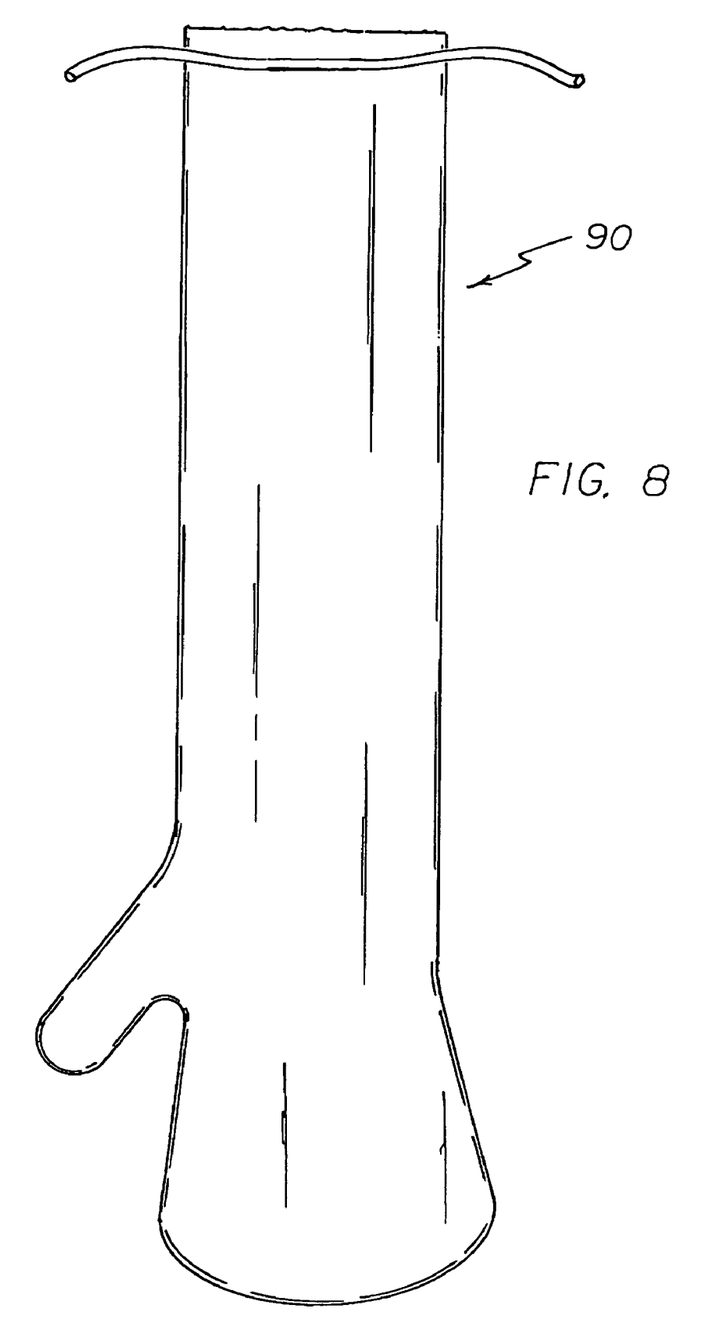
FIG. 8 illustrates a fourth alternate embodiment of the invention wherein the glove is a mitten.

FIG. 8 illustrates a fourth alternate embodiment of the invention. In this embodiment, the glove is a formed as a mitten 90. The preferred embodiment of the invention is illustrated as including a glove in FIGS. 1 through 6 with separate sections for a patient's fingers and thumb. It should be understood that the glove of this alternate embodiment of the present invention includes a mitten, a glove with a separate thumb section but no separate finger sections.

Figures 9, 10:
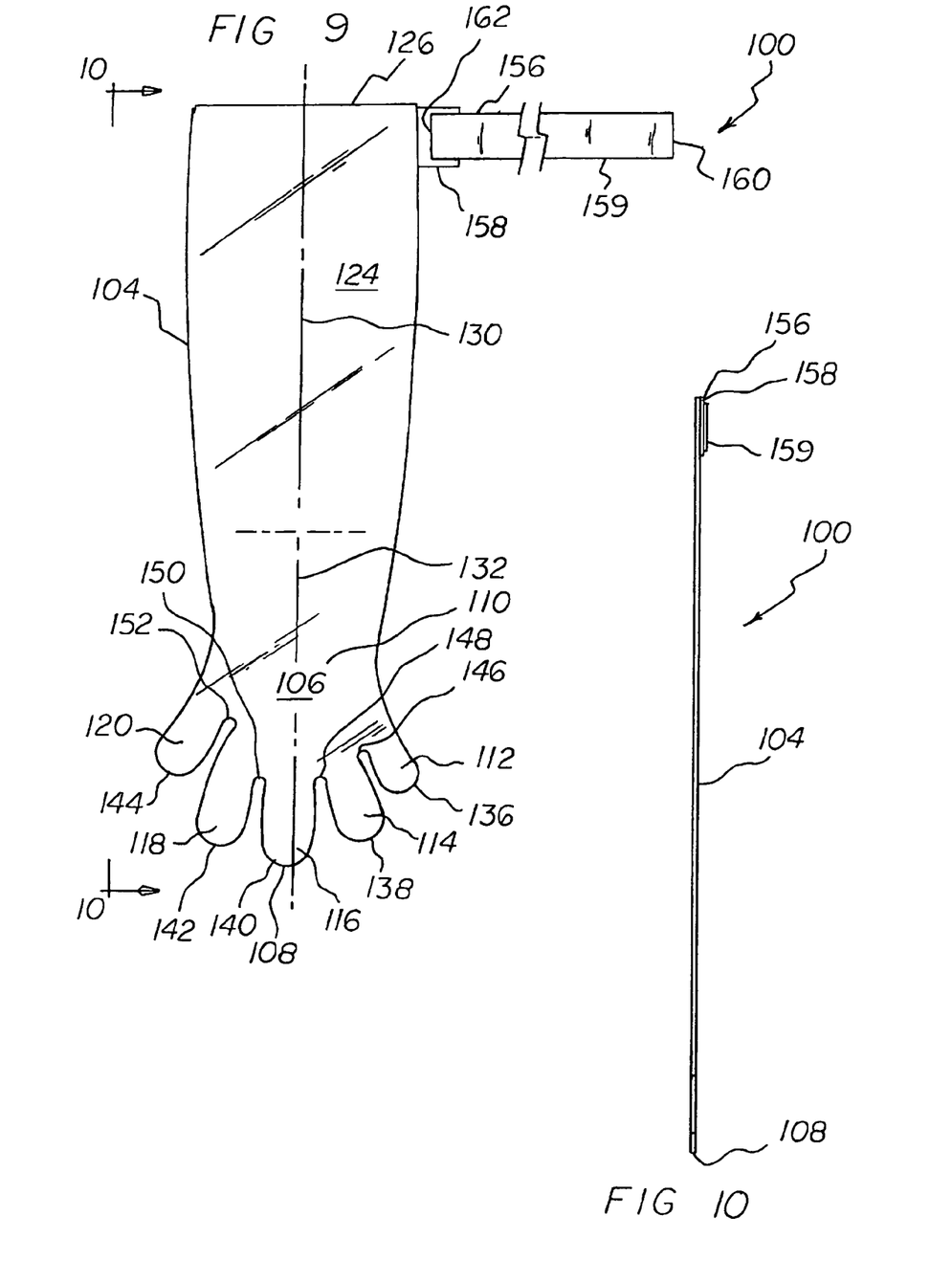
FIG. 9 is a front elevational view of a shower/glove system constructed in accordance with the final and preferred alternate embodiment of the invention.
FIG. 10 is a side elevational view of the system taken along line 10-10 of FIG. 9.

A final embodiment of the invention is illustrated in FIGS. 9 and 10. The shower/glove system 100 is for covering and protecting a hand and part of an arm of a wearer during showering and bathing. The covering and showering is done in a safe, sanitary, convenient and economical manner.

In this final embodiment, first provided is a glove 104. The glove has a distal portion 106 in the shape of a hand. The distal portion has a distal end 108. The distal portion is formed with a palm 110 and four fingers. The four fingers include a little finger 112, a fourth finger 114, a middle finger 116 and an index finger 118. The distal portion also includes a thumb 120. The distal portion is open for the receipt and passage of the hand of the wearer. The distal portion has a width varying along its length.

The glove of this final embodiment has a proximal portion 124 with a proximal end 126. The proximal portion is formed as an extension of the distal portion with an opening for the receipt and passage of the hand, forearm, elbow and a portion of the upper arm of the wearer. The proximal portion has a cross sectional configuration varying along its length. The cross sectional configuration of the proximal portion is greatest adjacent to the proximal end and least adjacent to the distal portion.

A common central axis has a proximal extent 130 extending through the proximal portion of the glove and a distal extent 132 extending through the distal portion of the glove including the middle finger. The proximal portion of the central axis of the glove has a length of between 12 and 18 inches. The distal portion of the central axis of the glove has a length of between 8 and 10 inches. Whereby, the proximal portion of the glove has a length between 150 percent and 175 percent of the length of the distal portion of the glove. The glove is fabricated of a transparent polyethylene with a thickness of between 0.003 inches and 0.012 inches.

In this final embodiment, the fingers of the glove each have a tip 136, 138, 140, 142 and the thumb of the glove has a tip 144. An arcuate recess 146, 148, 150 is formed between adjacent fingers and an arcuate recess 152 is formed between the thumb and the index finger. The thumb of the glove has a length of about 3 inches and the index finger has a length of about 5 inches whereby, the recess between the thumb and index finger forms a relief of about 1.27 inches adjacent to the palm. This allows a better fit for the hand into the glove and deeper penetration of an index finger and thumb of the wearer.

Lastly, in this final embodiment, a security seal 156 is provided at the proximal end of the proximal portion of the glove. The security seal includes a polyethylene tab 158 integrally formed with the glove. The tab is in a rectangular configuration having a width of 3.125 inches plus or minus 5 percent and a length of 2.375 inches plus or minus 8 percent. The security seal also includes a strap 159 fabricated of Coban™ brand elastic bandage. Coban is a trademark of Minnesota Mining and Manufacturing of St. Paul, Minn. for an elastic bandage. The tab and the strap are adapted to support manufacturing and joining of the strap to the tab to the glove. The strap has a free end 160 and an attached end 162 welded to the tab. The welding is done by heat at 90 degrees Centigrade plus or minus 10 degrees for about 5 seconds. The strap has a length of between 15 inches and 21 inches and a width of about 3 inches plus or minus 8 percent when unstretched. The strap has a semi-adhesive property for removably coupling the strap to itself when wrapped around the upper arm of a wearer during use to keep dry the hand, forearm and elbow and a portion of an upper arm of the wearer.

The closure mechanism or security seal of the present invention is of vital importance; the utility is practical due to the flexibility of the strap as opposed to theoretical utility. The present invention uses a bandage type material, preferably Coban™. This flexibility of the strap is vital in ensuring that the patient's bicep may flex normally during the bathing process. This feature is not obvious from the teachings of the prior art, nor is the type of material which is used in the present invention. Several types of material were tested. Certain types were found not usable for ensuring the proper functioning of the closure mechanism. Material containing Latex was found to be most effective in that water beads on such a material. Water is absorbed by non-Latex material leading to loosening of the wrap. This is clearly not taught in the prior art. The primary purpose of the present invention is to seal the opening where the arm goes in. The key is proper closing of the opening while still having a useful device. The present invention is dynamic in nature whereas the prior art merely provides a static barrier. Movement of the arm is less restricted due to the flexibility of the material.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

The dimensions and sizes specified herein are for illustrative purposes only. The glove is readily adapted to be manufactured in various sizes to accommodate adults of various sizes as well as for pediatric sizes.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A shower/glove system for covering and protecting a hand and part of an arm of a wearer during showering and bathing, the system comprising, in combination:
   a glove having a distal portion in the shape of a hand, the distal portion having a distal end, the distal portion being formed with a palm and four fingers including a little finger, a fourth finger, a middle finger, and an index finger, the distal portion also including a thumb, the distal portion being open for the receipt and passage of the hand of the wearer, the distal portion having a width varying along its length;
   the glove having a proximal portion with a proximal end, the proximal portion being formed as an extension of the distal portion with an opening for the receipt and passage of the hand, forearm, elbow and a portion of the upper arm of the wearer, the proximal portion having a cross sectional configuration varying along its length, the cross sectional configuration of the proximal portion being greatest adjacent to the proximal end and being least adjacent to the distal portion;
   a common central axis having a proximal extent extending through the proximal portion of the glove and a distal extent extending through the distal portion of the glove including the middle finger, the proximal portion of the central axis of the glove having a length of between 12 and 18 inches, the distal portion of the central axis of the glove having a length of between 8 and 10 inches whereby the proximal portion of the glove has a length between 150 percent and 175 percent of the length of the distal portion of the glove, the glove: being fabricated of a transparent polyethylene with a thickness of between 0.003 inches and 0.012 inches;
   the fingers each having a tip and the thumb having a tip, an arcuate recess between adjacent fingers and an arcuate recess between the thumb and the index finger, the thumb having a length of about 3 inches, the index finger having a length of about 5 inches, whereby the recess between the thumb and index finger forms a relief of about 1.27 inches adjacent to the palm for allowing a better fit for the hand into the glove and deeper penetration of an index finger and thumb of the wearer; and
   a security seal at the proximal end of the proximal portion of the glove, the security seal including a polyethylene tab with an interior end and an exterior end, the interior end integrally formed with the glove, the tab being in a rectangular configuration having a width of 3.125 inches plus or minus 5 percent and a length of 2.375 inches plus or minus 8 percent, a strap fabricated of elastic self-adhering medical bandaging tape, the tab and the strap adapted to support manufacturing and joining of the strap to the tab to the glove, the strap having a free end and an attached end welded to the exterior end of the tab, the welding being done by heat at 90 degrees Centigrade plus or minus 10 degrees for about 5 seconds, the strap having a length of between 15 inches and 21 inches and a width of about 3 inches plus or minus 8 percent when unstretched, the strap having a semi-adhesive property for removably coupling the strap to itself when wrapped around the upper arm of a wearer during use to keep dry the hand, forearm and elbow and a portion of an upper arm of the wearer.

* * * * *